United States Patent [19]
Aslund et al.

[11] Patent Number: 5,294,799
[45] Date of Patent: Mar. 15, 1994

[54] APPARATUS FOR QUANTITATIVE IMAGING OF MULTIPLE FLUOROPHORES

[76] Inventors: Nils R. D. Aslund, Skontorpsvägen 126, 9 tr, S-121 65 Johanneshov; Kjell S. Carlsson, Malmbodavägen 17, S-186 42 Vallentuna, both of Sweden

[21] Appl. No.: 11,881

[22] Filed: Feb. 1, 1993

[51] Int. Cl.$^5$ ............................. G01N 21/64
[52] U.S. Cl. .................. 250/458.1; 250/459.1
[58] Field of Search ............ 250/458.1, 459.1, 461.1, 250/462.2; 356/317, 318

[56] References Cited

U.S. PATENT DOCUMENTS

| | | | |
|---|---|---|---|
| 4,603,209 | 7/1986 | Tsien et al. | 548/236 |
| 4,628,026 | 12/1986 | Gardell et al. | 435/7 |
| 4,680,275 | 7/1987 | Wagner et al. | 436/518 |
| 4,807,990 | 2/1989 | Keefer | 356/28.5 |
| 4,833,332 | 5/1989 | Robertson et al. | 250/458.1 |
| 4,849,362 | 7/1989 | DeMarinis et al. | 436/63 |
| 4,937,457 | 6/1990 | Mitchell | 250/458.1 |
| 5,032,714 | 7/1991 | Takahashi et al. | 250/213 VT |
| 5,047,321 | 9/1991 | Loken et al. | 435/6 |
| 5,049,673 | 9/1991 | Tsien et al. | 546/107 |
| 5,212,386 | 5/1993 | Gratton et al. | 250/458.1 |

*Primary Examiner*—Paul M. Dzierzynski
*Assistant Examiner*—Richard Hanig
*Attorney, Agent, or Firm*—Schneck & McHugh

[57] ABSTRACT

A quantitative fluorometer for multiple fluorophores having a separate time-modulated beam of excitation light for each fluorescent target. Each beam is synchronized with a separate lock-in amplifier. The fluorophores are simultaneously excited and the combined fluorescent emission is resolved into components corresponding to each fluorophore. Confocal scanning means are used to excite and detect fluorescent emission from locations throughout a volume. The location specific output of each amplifier is stored in a computer which resolves the emission into the components corresponding to each fluorophore. The location specific data may be further processed or visually displayed.

23 Claims, 5 Drawing Sheets

LOCK-IN AMPLIFIER 1

LOCK-IN AMPLIFIER 2

APPARATUS FOR QUANTITATIVE IMAGING OF MULTIPLE FLUOROPHORES

FIELD OF THE INVENTION

This invention relates to quantitative microfluorometry and more particularly to a device for quantitative microfluorometry in which one or more fluorophores are quantitated by simultaneous excitation at two or more wavelengths.

BACKGROUND ART

Recent development of fluorescent indicator dyes for biologically important intracellular components has made it possible to follow the time-dependent distribution of these components in intact cells. For example, see U.S. Pat. Nos. 5,049,673, 4,849,362 and 4,603,208.

The emitted fluorescent radiation from a fluorophore in response to excitation at a single wavelength generally represents a broad band of wavelengths. The spectra of emissions from different fluorophores will generally overlap. This is a major problem in many practical applications involving multiple fluorophores, making quantitative measurements of the individual fluorophores difficult or impossible.

Fluorophores absorb excitation radiation at more than one wavelength. The absorption spectra of different fluorophores may thus also overlap. In summary, in the past fluorescent detection has been primarily limited to cases where the absorption spectra overlap only to a small extent or where the wavelength regions of spectral overlap of the emissions can be suppressed by optical filtering. In the latter case separation is achieved at the expense of losing valuable signal intensity.

When a fluorophore is excited by light having a sinusoidally modulated intensity the fluorescence emitted is also sinusoidally modulated. The modulation frequencies are the same but the phase of the emitted fluorescence is shifted by an amount related to the lifetime of the fluorophore's excited state. U.S. Pat. No. 4,937,457 to Mitchell discloses a frequency domain spectrofluorometer which uses a single wavelength of excitation modulated at multiple harmonically related phase-locked frequencies to simultaneously determine the spectral response and phase shift of a single fluorophore to the entire range of modulation frequencies employed. The data produced is used to determine the fluorescence lifetime of a fluorophore.

In U.S. Pat. No. 5,032,714 to Takahashi et al. a light waveform measuring device is used for measuring the lifetime of fluorescent light produced due to pulsed laser excitation. Two laser beams of different frequencies, at least one of which is pulsed, are used to produce a single-frequency pulsed beam selected from the sum frequency mixing of the beams. The output beam is pulsed at the same rate as the pulsed input beam which is used to trigger a single-photon detector or streak camera. The detector is thereby synchronized to the exciting beam.

Identification and discrimination of multiple fluorophores in a sample is disclosed in U.S. Pat. No. 5,047,321 to Loken et al. Each component must have a distinguishable characteristic peak emission wavelength at which a detector is set. Fluorophores may be excited with a single wavelength or multiple wavelengths, but detection occurs in regions where the peak emission spectra do not overlap.

In U.S. Pat. No. 4,628,026 to Gardell et al. an automated system for the sequential and alternate irradiation of a specimen by two distinguishable wavelengths of light is disclosed. The system classifies specimens based on the quotient of the fluorescent light intensities sequentially received from the specimen in response to the two excitation wavelengths.

Simultaneous recording of multiple fluorophores excited by a single wavelength using spectral filtering or separation is disclosed in U.S. Pat. No. 4,833,332 to Robertson, Jr. et al. The fluorophores which have overlapping emission spectra are distinguished by the ratio of their emissions transmitted by two spectral filters having complementary transmission spectra. The system is not capable of quantitative determinations.

The prior art devices which measure fluorescence at only one peak emission wavelength are unable to simultaneously quantitate multiple fluorophores using the total emission from each fluorophore. Those devices which rely on spectral separation to distinguish multiple fluorophores are unable to separate the total contribution of each fluorophore from the combined emission spectrum detected.

It is an object to provide an improved microfluorometer capable of simultaneously quantitating multiple fluorophores with greater efficiency.

It is another object of the present invention to provide an improved microfluorometer which simultaneously utilizes the entire emissions of multiple fluorophores or the entire emission spectra except possibly for minor parts.

It is a further object to provide an improved microfluorometer capable of separating the contribution from fluorophores having overlapping absorption spectra from the combined emission spectrum detected.

SUMMARY OF THE INVENTION

The above objects have been achieved in a microfluorometer which simultaneously excites one or more fluorophores with two or more wavelengths. The intensity of the excitation at each wavelength is time modulated at a separate frequency and a separate frequency-locked phase sensitive detector for each modulation frequency allows discrimination of the contribution from the individual spectra corresponding to each fluorophore. In the preferred embodiment each excitation wavelength is chosen to predominantly excite one of the fluorophores. A separate lock-in amplifier is synchronized to the modulation frequency of each excitation wavelength. In one preferred embodiment dual phase lock-in amplifiers are used with the in-phase channel tuned to a phase position near to that of the fluorophore predominantly excited by that wavelength. Using the in-phase and quadrature outputs of each amplifier, all components of the combined emission spectrum may be separated.

The phase angles of the emission spectra are determined from data obtained in regions where only one of the fluorophores is present. These regions may be identified by direct observation or by analysis of the data set from the entire specimen.

In a second preferred embodiment a single phase lock-in amplifier is used for each excitation wavelength. The phase position of the amplifier is tuned to the position that gives a maximum output value for the fluorescence emitted by the predominantly excited fluorophore. Using single phase amplifiers, the emission spectra corresponding to each predominantly excited fluorophore may be discriminated.

An advantage of the microfluorometer of the present invention is that the entire emissions of the fluorophores are simultaneously measured.

Another advantage is that the contribution of each fluorophore may be separated from the combined emission spectrum even if the absorption spectra overlap.

A further advantage is that multiple fluorophores are simultaneously quantitated with greater efficiency.

DETAILED DESCRIPTION OF THE PREFERRED EMBODIMENT

Figure 1:
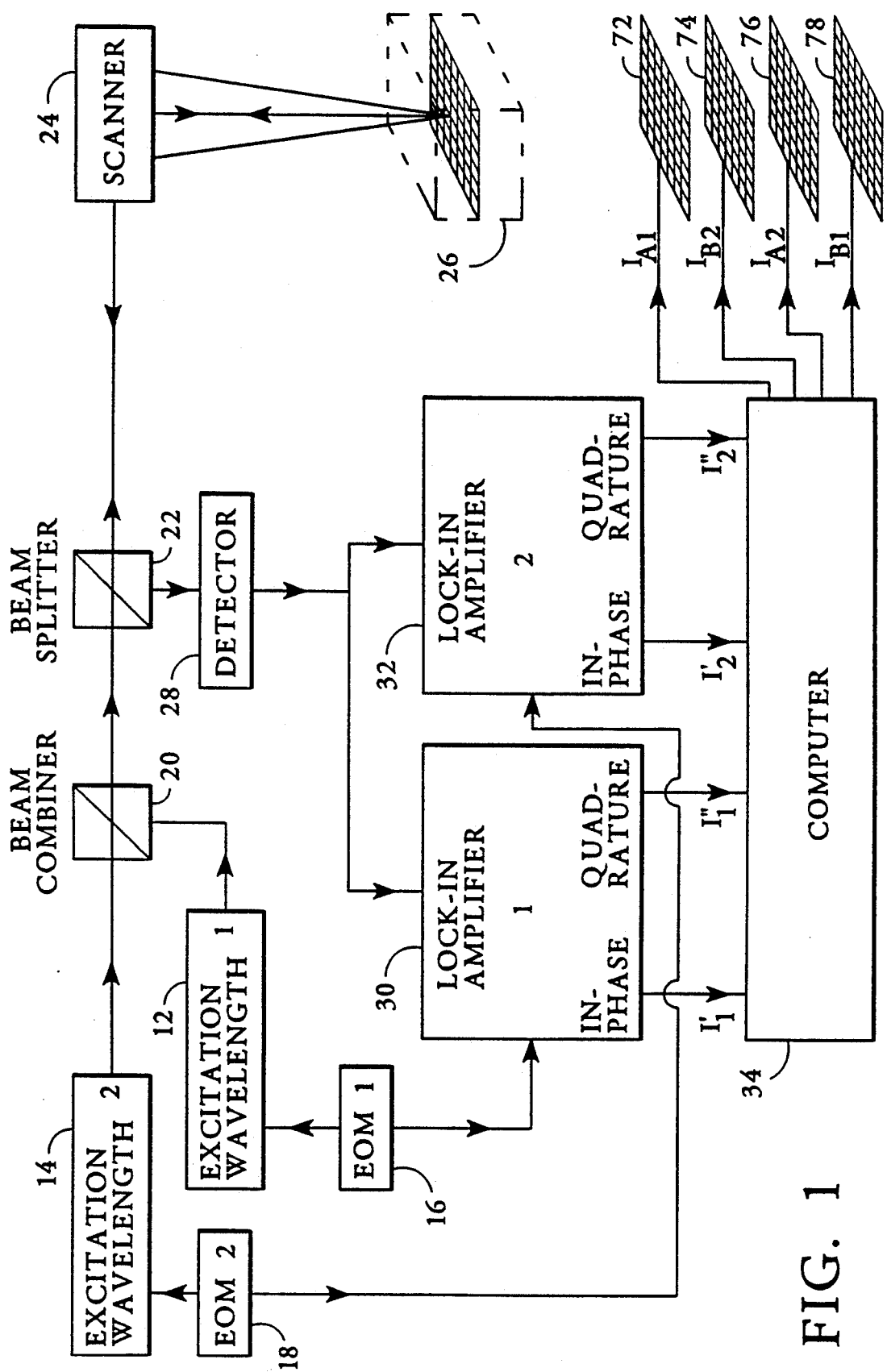
FIG. 1 is a schematic block diagram of a quantitative microfluorometer in accordance with the present invention.
Figure 2A:
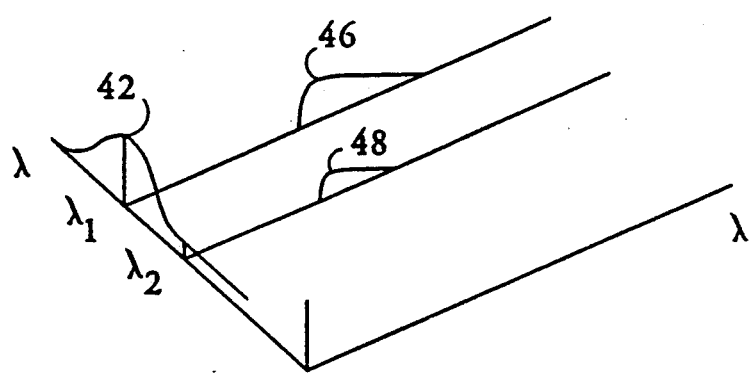
FIGS 2a-d are plots showing the individual spectral components of a combined emission spectrum.
Figure 2B:
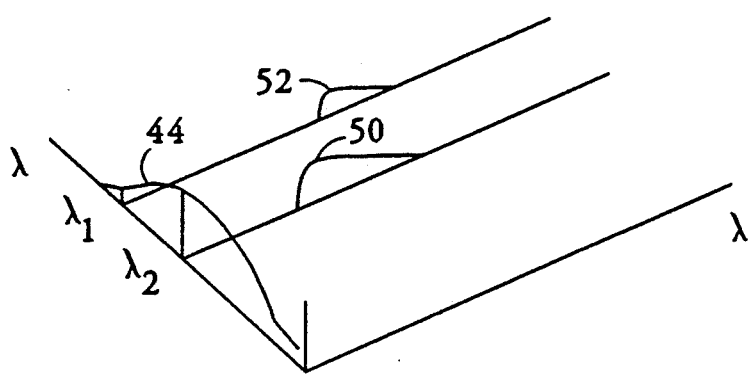
Figure 2C:
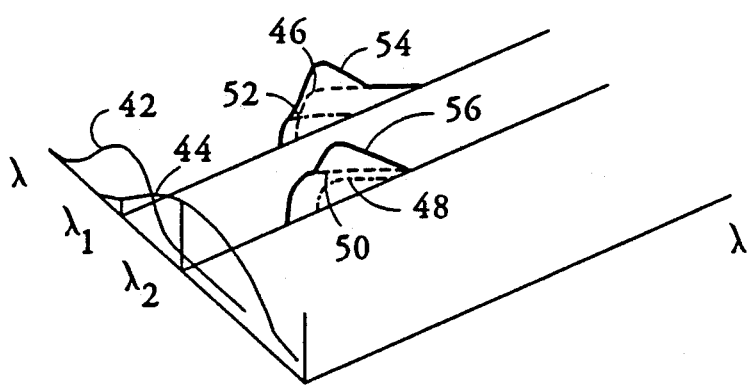
Figure 2D:
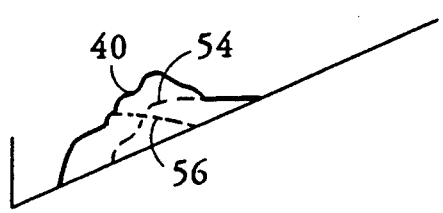

With reference to FIG. 1, a schematic block diagram of a preferred embodiment of the quantitative microfluorometer employing two excitation wavelengths and two dual phase lock-in amplifiers is shown. Monochromatic excitation light of different wavelengths is supplied by a pair of light sources 12 and 14. In the preferred embodiment, light sources 12 and 14 are separate diode lasers although any source of continuous electromagnetic radiation capable of being time-modulated in intensity may be used. The intensity of light source 12 is controlled by a modulator 16 operating at a sinusoidal frequency $\nu 1$. In similar fashion, light source 14 is controlled by a second modulator 18 operating at a separate frequency $\nu 2$. In preferred embodiments, modulators 16 and 18 are electro-optical modulators or acousto-optical modulators operating at frequencies up to 50 Mhz. Any modulator capable of operating at frequencies preferably at least two times greater than the sampling frequency of the microfluorometer may be substituted. Individual light beams from light sources 12 and 14 are combined in a beam combiner 20. The combined beam passes through a beamsplitter 22 which transmits light at the excitation wavelengths $\lambda 1$ and $\lambda 2$. A scanner 24 sequentially directs the combined beam to locations within a sample 26. In the preferred embodiment, scanner 24 is a confocal laser microscope although any device capable of focusing excitation radiation at, and collecting emitted radiation from, a discrete location in sample 26 may be used. Sample 26 may be any light-transmitting object containing one or more fluorophores. Such objects include biological cells and two dimensional gels used for separating compounds.

The combined fluorescence emitted in response to excitation at the focal point of scanner 24 is collected by scanner 24 and directed to beamsplitter 22 which deflects emitted fluorescence to a detector 28. Detector 28 may be any device which produces a signal in response to the photons emitted by the fluorophores. Photomultipliers which convert photons into electrical signals are examples of such devices. The signal produced by detector 28 is sent to a pair of lock-in amplifiers 30 and 32. Lock-in amplifier 30 is synchronized with the modulation frequency $\nu 1$ imposed on light source 12 by modulator 16. Similarly lock-in amplifier 32 is synchronized with the modulation frequency $\nu 2$ imposed on light source 14 by modulator 18. In the preferred embodiment lock-in amplifiers 30 and 32 are dual phase amplifiers producing two outputs which represent amplitudes of the recorded waveform at phase positions that are 90° apart. The outputs from lock-in amplifiers 30 and 32 are sent to a computer 34. Computer 34 stores the inputs corresponding to each discrete location in sample 26 in a location specific manner and mathematically reconstructs the individual spectral components corresponding to the excitation of each fluorophore by each wavelength. In the preferred embodiments, computer 34 is a digital computer and the outputs from amplifiers 30 and 32 are digitized, before storage, by conventional analog to digital converters.

Referring now to FIGS. 2a-d, the curves show the individual spectral components of a combined emission spectrum emitted by two fluorophores in response to excitation by two wavelengths. $\lambda 1$ and $\lambda 2$ are selected by examining the absorption spectra 42 and 44 of fluorophores A and B respectively. $\lambda 1$ is chosen to predominantly excite fluorophore A, while $\lambda 2$ is chosen to predominantly excite fluorophore B. Fluorophore A produces a main fluorescent emission spectrum 46 ($I_{A1}$) in response to $\lambda 1$ and a smaller cross-excited fluorescent emission spectrum 48 ($I_{A2}$) in response to $\lambda 2$. This results from the fact that absorption spectra 42 and 44 overlap. Similarly fluorophore B produces a main fluorescent emission spectrum 50 ($I_{B2}$) in response to $\lambda 2$ and a smaller cross excited fluorescent emission spectrum 52 in response to $\lambda 1$. Excitation at wavelength $\lambda 1$ produces a combined response 54 which is the sum of fluorophore A main response 46 and fluorophore B cross-excited response 52 ($I_{A1}+I_{B1}$). Similarly, excitation at wavelength $\lambda 2$ produces a combined response 56 consisting of fluorophore B main response 50 and fluorophore A cross-excited response 48 ($I_{B2}+I_{A2}$). A combined emission spectrum 40, in response to excitation by $\lambda 1$ and $\lambda 2$, is composed of the sum of emission spectra 46, 48, 50 and 52 ($I_{A1}+I_{A2}+I_{B1}+I_{B2}$).

Figure 3A:
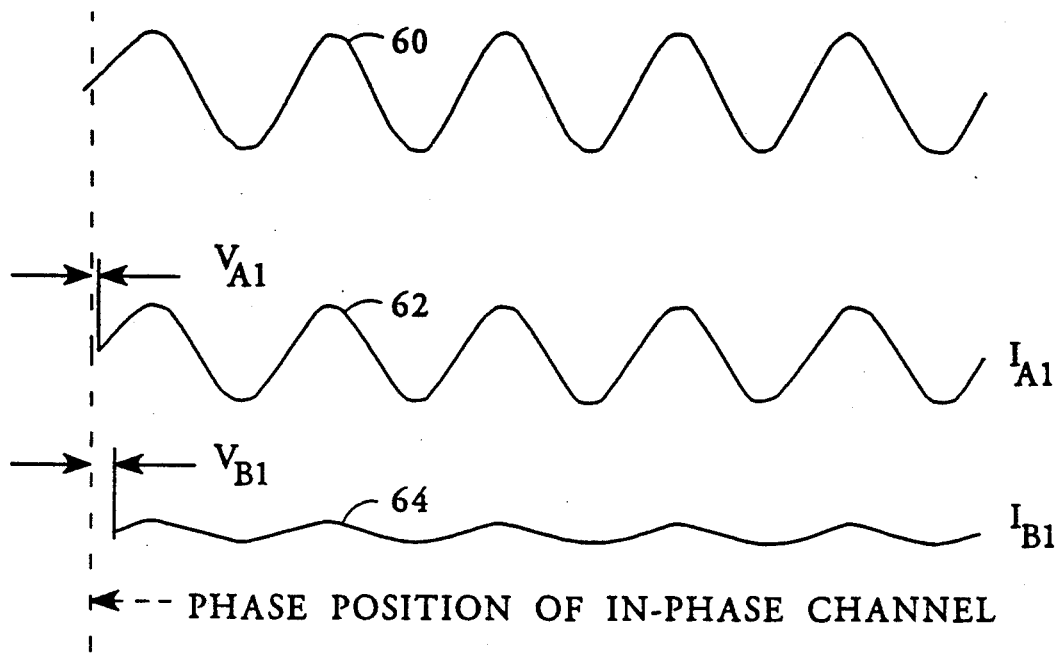
FIGS. 3(a) (b) are diagrammatic representations of the phase relation between the modulated excitation wavelength and the modulated fluorescent emissions from two fluorophores for each of the lock-in amplifiers.
Figure 3B:
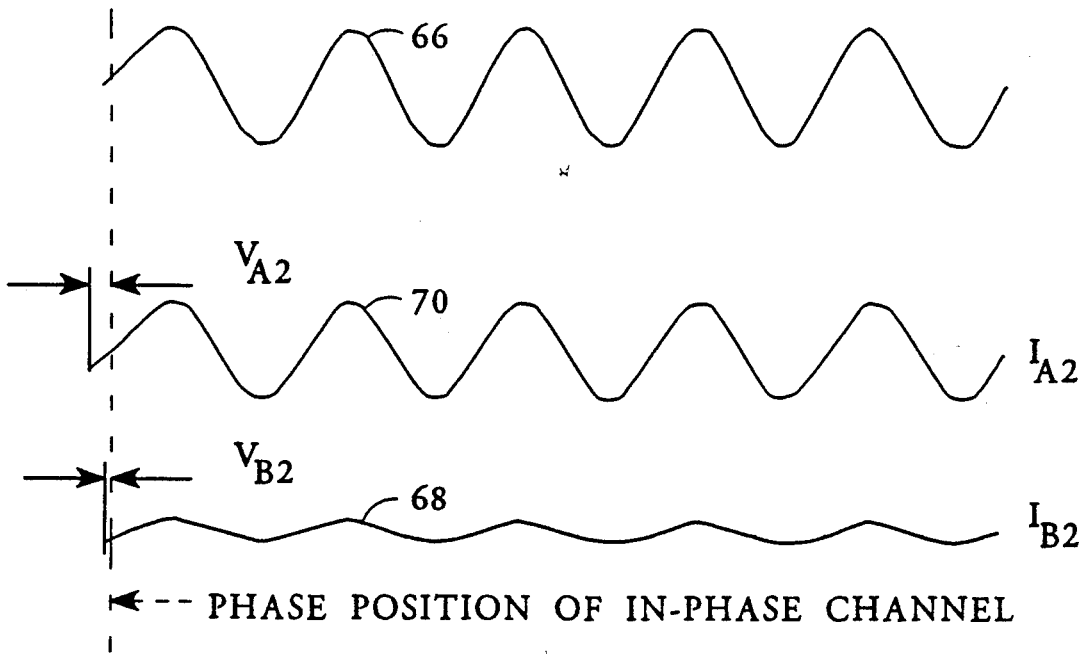

Referring now to FIGS. 3a and 3b, the phase relationship between waveforms of the modulated excitation beams and the corresponding emitted fluorescence is shown. The intensity modulation of the beam having excitation wavelength $\lambda 1$ is represented by a sinusoidal waveform 60. Fluorophore A responds to $\lambda 1$ with a sinusoidally modulated fluorescent main signal 62. Fluorophore B also responds to $\lambda 1$ with a smaller modulated fluorescent cross-excited signal 64. The frequencies of excitation signal 60 and fluorescent signals 62 and 64 are the same and will be captured by lock-in amplifier 30 which is synchronized with the modulation frequency $\nu 1$ of $\lambda 1$. The phase of the emitted fluorescence waveform however will differ from that of the excitation waveform. The phase relationship between the emitted fluorescence waveform and the excitation waveform is dependent upon the fluorescent relaxation time of the individual fluorophores and on the modulation frequency. Lock-in amplifier 32 is synchronized with the modulation frequency $\nu_2$ of $\lambda_2$. Fluorophore B, which is predominantly excited by $\lambda_2$, emits a modulated fluorescent main signal 68 while fluorophore A emits a smaller modulated fluorescent cross excited signal 70. Fluorescent signals 68 and 70 have the same frequency as excitation 66 and are captured by lock-in amplifier 32. The phases of the emitted fluorescent signals 68 and 70 however will differ from the phase of excitation 66.

Figure 4:
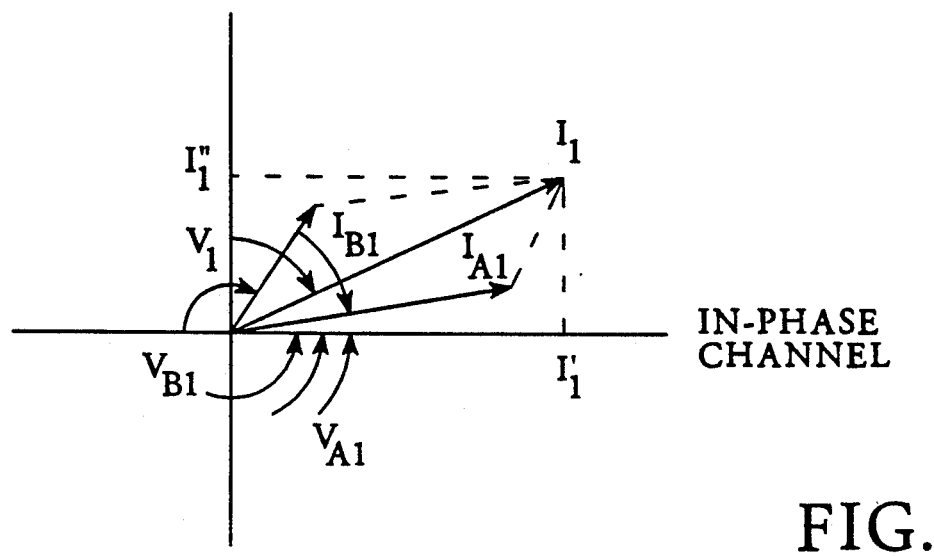
FIG. 4 is a vector diagram of the phase angles of the components of the output of dual phase lock-in amplifier 1.
Figure 5:
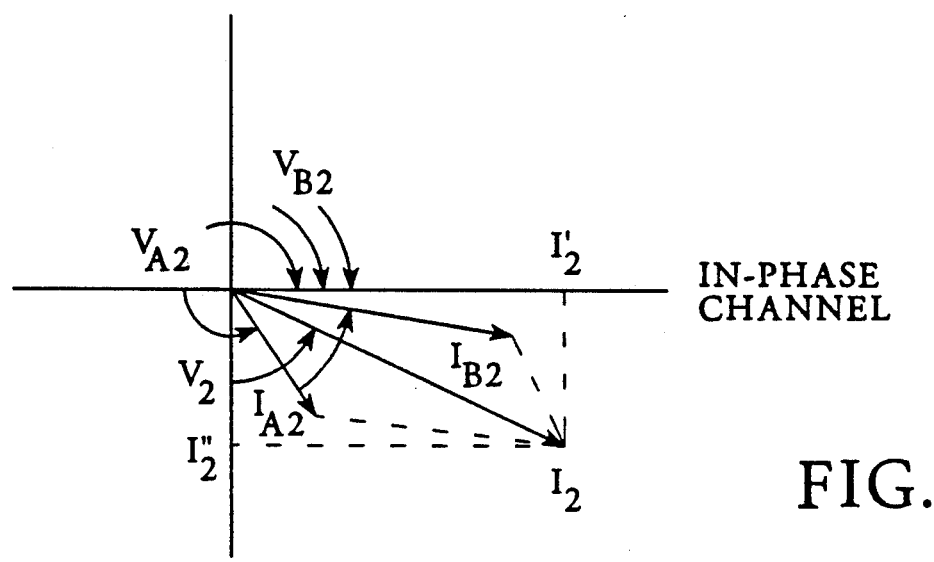
FIG. 5 is a vector diagram showing the phase relationship of the components of the output of dual phase lock-in amplifier 2.

Referring now to FIGS. 4 and 5, the vector components and phase angles of the in-phase and quadrature channels of lock-in amplifiers 30 and 32 respectively are shown. For amplifier 30 the output of the in-phase channel is represented by the quantity $I_1'$ and the output of the quadrature channel is represented by the quantity $I_1''$. The input to amplifier 30 is represented by a vector of amplitude $I_1$ at a phase angle to the in-phase channel of $V_1$. This is composed of the vector sum of the signals corresponding to each fluorophore represented by $I_{A1}$ at an angle $V_{A1}$ for fluorophore A and $I_{B1}$ at angle $V_{B1}$ for fluorophore B. Similar notation is used in FIG. 5 with the subscript 2 replacing the subscript 1 for the components of lock-in amplifier 32. The following equations are used in computer 34 to resolve the outputs of amplifiers 30 and 32 into the component vectors for fluorophores A and B:

$$I_1' = I_1 \cos V_1 = I_{A1} \cos V_{A1} + I_{B1} \cos V_{B1}$$

$$I_2' = I_2 \cos V_2 = I_{A2} \cos V_{A2} + I_{B2} \cos V_{B2} \quad \text{(E1)}$$

$$I_1'' = I_1 \sin V_1 = I_{A1} \sin V_{A1} + I_{B1} \sin V_{B1}$$

$$I_2'' = I_2 \sin V_2 = I_{A2} \sin V_{A2} + I_{B2} \sin V_{B2}$$

The phase position of the in-phase channel is tuned to be close to the position that gives a maximum value for the output from the predominantly excited fluorophore. Lock-in amplifier 30 is thus tuned to detect signals from fluorophore A predominantly while lock-in amplifier 32 is tuned to detect signals from fluorophore B predominantly.

In order to determine angles $V_{A1}$ and $V_{A2}$ it is necessary to collect data from a region where fluorophore A is present and fluorophore B is not. In these regions:

$$\tan V_{A1} = I_1''/I_1'$$

$$\tan V_{A2} = I_2''/I_2'$$

These regions may be determined by direct observation or by searching the data set corresponding to the locations throughout specimen 26 which are digitally stored in computer 34 in a location specific manner. Regions where fluorophore A is present and fluorophore B is not may be identified by the fact that $I_2'/I_1'$ is minimized in these regions.

$V_{B1}$ and $V_{B2}$ may be determined in similar fashion from regions where fluorophore B is present and fluorophore A is not. In those regions:

$$\tan V_{B1} = I_1''/I_1'$$

$$\tan V_{B2} = I_2''/I_2'$$

Regions in the data set where fluorophore B is present and fluorophore A is not are characterized by the fact that $I_1'/I_2'$ is minimized.

Having determined values for $V_{A1}$, $V_{B1}$, $V_{B2}$ and $V_{A2}$, computer 34 is able to solve the four simultaneous equations (E1) having four unknowns, $I_{A1}$, $I_{A2}$, $I_{B1}$ and $I_{B2}$, using conventional numerical techniques. In the preferred embodiments, the derived quantities, $I_{A1}$, $I_{A2}$, $I_{B1}$ and $I_{B2}$, representing the individual components of combined emission spectrum 40 are digitally stored in the memory of computer 34 for each location scanned in specimen 26. The data may be output by computer 34 as displayed images 72, 74, 76 and 78, shown in FIG. 1 corresponding to components $I_{A1}$, $I_{B2}$, $I_{A2}$ and $I_{B1}$ respectively, or used for further processing.

Figure 6:
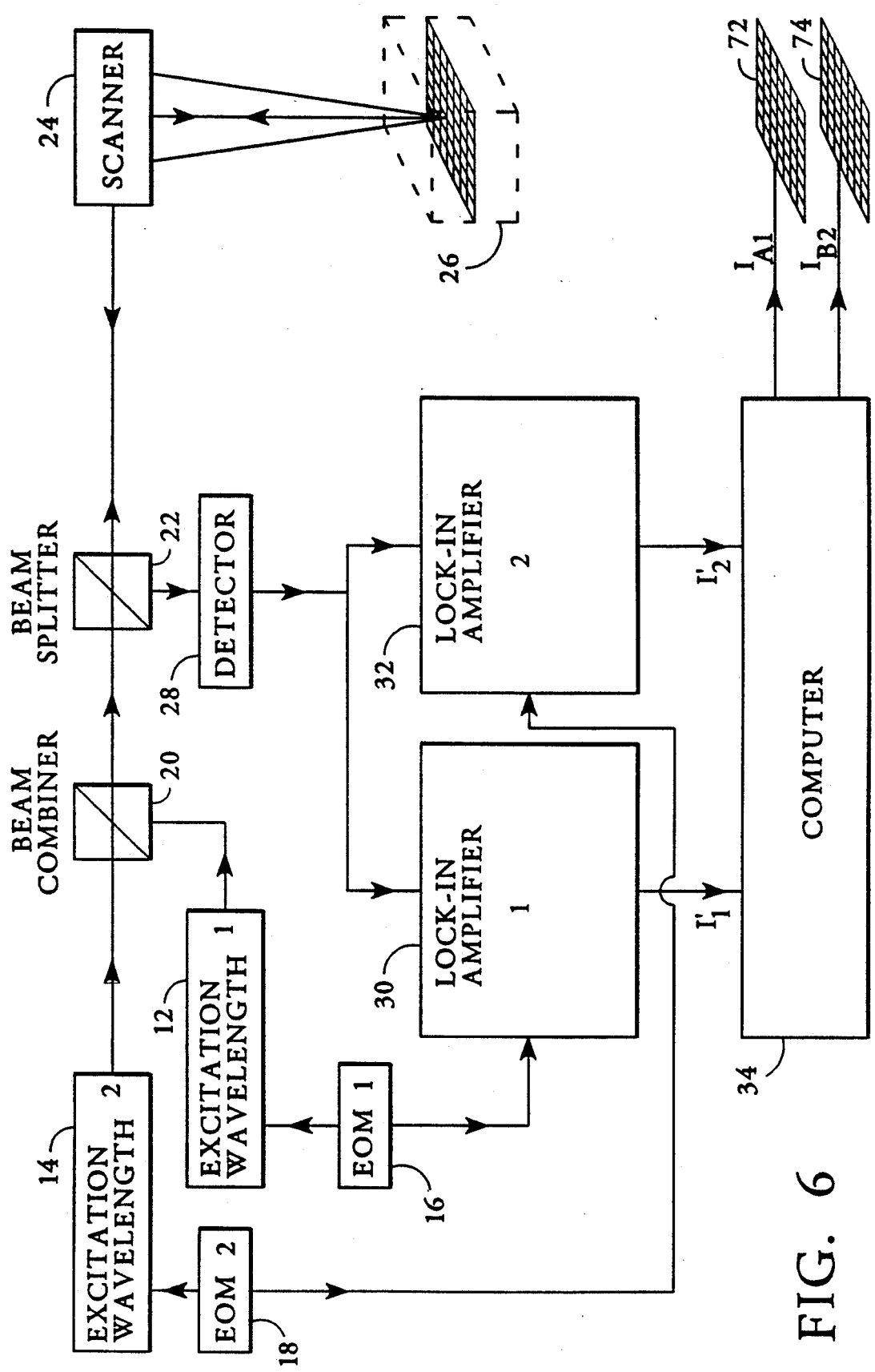
FIG. 6 is a schematic block diagram of a preferred embodiment of the present invention using single phase lock-in amplifiers.

Referring now to FIG. 6, a schematic block diagram of a second preferred embodiment employing single phase lock-in amplifiers is shown. When specimen 26 contains two fluorophores which have different relaxation times, the waveforms corresponding to the fluorescent excitation generated by the fluorophores will differ in phase. The phase position of lock-in amplifier 30, which picks up emission predominantly from fluorophore A, is tuned to the position which cancels out the contribution from the waveform generated by fluorophore B. The phase position of lock-in amplifier 32, which picks up emission predominantly from fluorophore B, is tuned to the position that cancels out the contribution from the waveform generated by fluorophore A. Regions where one fluorophore is present and the other is not are determined by direct observation.

If fluorophores A and B do not have different relaxation times, lock-in amplifiers 30 and 32 are tuned to the positions which give maximum output from the predominantly excited fluorophore. Regions where a single fluorophore only is present can be determined by scanning the data set for minimum values of the quotients $I_2'/I_1'$ and $I_1'/I_2'$. The underlying assumption is that for each fluorophore the cross-excited emission is proportional to the main emission. This procedure may also be followed if the two fluorophores have different relaxation times. When single phase lock-in amplifiers are used, computer 34 is only able to derive the quantities $I_{A1}$ and $I_{B2}$, representing individual components of combined emission spectrum 40. The data may be output by computer 34 as displayed image 72 for $I_{A1}$ from fluorophore A and 74 for $I_{B2}$ from fluorophore B.

The ability of the present invention to quantitate multiple fluorophores simultaneously may be utilized in a variety of applications. These include the quantitative analysis of fluorescently labeled compounds which have been electrophoretically separated. For example the individual bases in a DNA sequencing. Additionally the kinetics of reactions involving fluorescently labeled compounds in intact cells may be followed. It may also be possible to perform image segmentation in three dimensions. For example regions where the fluorescent relaxation times take specific values may be extracted from recorded images. This would open a completely new way to analyze and quantify microscopic structures in three dimensions.

As an example, we have used fluorophores of Lucifer Yellow at 458 nm and TRITC (tetramethyl rhodamine isotio-cyanate) at 514 nm. These fluorophores were modulated at 0.7 MHz and 0.9 MHz respectively using two argon-ion lasers of about 1 watt output power each. The pixel sampling rate was 100 KHz.

We claim:

1. A device for quantifying one or more fluorescent targets by excitation with electromagnetic radiation of multiple discrete wavelengths comprising:

means for directing dual beams of continuous electromagnetic radiation, each beam having a discrete wavelength, said beams impinging on a single location where fluorescent targets are present causing excitation thereof;

means for modulating the intensity of each of said beams at separate modulation frequencies to give each of said beams a specific time modulated waveform;

means for detecting the combined fluorescent emission from said targets in response to said excitation; and demodulation means for extracting the contributions corresponding to each of said targets from said detected combined fluorescent emission, thereby quantifying said targets.

2. The device of claim 1 wherein each of said beams is produced by a separate diode laser, each of said diode lasers being modulated in intensity with a separate frequency.

3. The device of claim 1 wherein said means for modulating the intensity of each of said beams includes a separate modulator for each beam.

4. The device of claim 3 wherein said modulator is an electro-optical modulator.

5. The device of claim 3 wherein said modulator is an acousto-optical modulator.

6. The device of claim 1 wherein said demodulation means includes signal extracting means for each target, said signal extracting means being specific for signals having the same frequency as the modulation frequency of a beam exciting said target, the output of said signal extracting means being specific to a particular phase position of the modulated waveform.

7. The device according to claim 6 wherein said signal extracting means includes a signal phase lock-in amplifier for each target, said amplifier being synchronized with the modulating frequency of a corresponding beam.

8. The device according to claim 7 wherein the phase position of said single phase amplifier is tuned to a position such that the contribution to the combined waveform from one of said targets is zero.

9. The device according to claim 7 further comprising scanning means having a sampling rate for detecting said combined fluorescent emission at locations within a scanning plane and wherein the phase position of said single phase amplifier is tuned to the position which maximizes the output of said amplifier from one of said targets.

10. The device according to claim 9 wherein said demodulation means includes analog-to-digital conversion means for digitizing the output from said lock-in amplifiers, and digital storage means for storing said digital outputs.

11. The device according to claim 10 wherein said digital storage means includes a memory capable of storing recorded data from all locations within said scanning plane in a location specific manner.

12. The device according to claim 11 further comprising confocal means for detecting said combined fluorescent emission at locations throughout a volume.

13. The device according to claim 6 wherein said signal extracting means includes a dual phase lock-in amplifier for each target.

14. The device according to claim 13 further comprising scanning means for detecting said combined fluorescent emission at locations within a scanning plane or planes.

15. The device according to claim 13 wherein said demodulation means includes analog-to-digital conversion means for digitizing the output from said lock-in amplifiers, and digital storage means for storing said digital outputs.

16. The device according to claim 15 wherein said digital storage means includes a memory capable of storing recorded data from all locations within said scanning plane or planes in a location specific manner.

17. The device according to claim 16 further comprising confocal means for detecting said combined fluorescent emission at locations throughout a volume.

18. A system for performing quantitative microfluorometry comprising:

confocal means for directing dual beams of light, each of said beams having a discrete wavelength, said beams impinging on a location where fluorescent targets are present causing excitation thereof;

means for modulating each of said beams with a separate modulation frequency;

scanning means having a sampling rate for detecting the combined fluorescent emission from said targets at locations in a scanning plane or planes in response to said excitation;

phase and frequency discriminating means for extracting the individual emissions corresponding to each of said targets from said detected combined fluorescent emission, thereby quantifying said targets;

means for converting the discriminated emissions from said targets to location specific signals; and means for storing said location specific signals in a memory.

19. The system of claim 18 wherein said confocal means for directing dual beams of light includes two diode lasers with different output frequencies.

20. The system of claim 18 wherein said confocal means includes electro-optical modulators for modulating said beams.

21. The system of claim 18 wherein said confocal means includes acousto-optical modulators for modulating said beams.

22. The system of claim 18 wherein said phase and frequency discriminating means includes a dual phase lock-in amplifier for each of said modulated beams.

23. The system of claim 18 wherein said phase and frequency discriminating means includes a single phase lock-in amplifier for each of said modulated beams.

* * * * *